(12) United States Patent
Toren-Herrinton et al.

(10) Patent No.: US 8,469,897 B2
(45) Date of Patent: Jun. 25, 2013

(54) METHOD AND SYSTEM FOR TRACKING QUALITY OF LIFE IN PATIENTS WITH ANGINA

(75) Inventors: Seth Toren-Herrinton, Mountain View, CA (US); Harish Krishnaswamy, Mountain View, CA (US); Rajiv Venkata, Sherman Oaks, CA (US); Jason Sutor, Sunnyvale, CA (US)

(73) Assignee: Pacesetter, Inc., Sylmar, CA (US)

( * ) Notice: Subject to any disclaimer, the term of this patent is extended or adjusted under 35 U.S.C. 154(b) by 1653 days.

(21) Appl. No.: 11/872,669

(22) Filed: Oct. 15, 2007

(65) Prior Publication Data

US 2009/0099467 A1 Apr. 16, 2009

(51) Int. Cl.
 *A61B 5/00* (2006.01)
(52) U.S. Cl.
 USPC .......................................... 600/508
(58) Field of Classification Search
 USPC .......................................... 600/508
 See application file for complete search history.

(56) References Cited

U.S. PATENT DOCUMENTS

| | | | |
|---|---|---|---|
| 5,113,869 A | 5/1992 | Nappholz et al. |
| 5,135,004 A | 8/1992 | Adams et al. |
| 5,199,428 A | 4/1993 | Obel et al. |
| 5,203,326 A | 4/1993 | Collins |
| 5,251,621 A | 10/1993 | Collins |
| 5,313,953 A | 5/1994 | Yomtov et al. |
| 5,388,578 A | 2/1995 | Yomtov et al. |
| 5,497,780 A | 3/1996 | Zehender |
| 5,531,768 A | 7/1996 | Alferness |
| 6,016,443 A | 1/2000 | Ekwall et al. |
| 6,021,350 A | 2/2000 | Mathson |
| 6,108,577 A | 8/2000 | Benser |
| 6,112,116 A | 8/2000 | Fischell et al. |
| 6,115,628 A | 9/2000 | Stadler et al. |
| 6,128,526 A | 10/2000 | Stadler et al. |
| 6,233,486 B1 | 5/2001 | Ekwall et al. |
| 6,256,538 B1 | 7/2001 | Ekwall |
| 6,264,606 B1 | 7/2001 | Ekwall et al. |
| 6,272,379 B1 | 8/2001 | Fischell et al. |
| 6,324,421 B1 | 11/2001 | Stadler et al. |
| 6,368,284 B1 | 4/2002 | Bardy |
| 6,381,493 B1 | 4/2002 | Stadler et al. |
| 6,468,263 B1 | 10/2002 | Fischell et al. |
| 6,501,983 B1 | 12/2002 | Natarajan et al. |
| 6,609,023 B1 | 8/2003 | Fischell et al. |
| 6,937,899 B2 | 8/2005 | Sheldon et al. |
| 7,123,965 B2 | 10/2006 | Condie et al. |
| 2002/0143262 A1 | 10/2002 | Bardy |
| 2002/0143263 A1 | 10/2002 | Shusterman |

(Continued)

FOREIGN PATENT DOCUMENTS

| | | |
|---|---|---|
| EP | 0450341 | 10/1991 |
| EP | 1164933 B1 | 5/2006 |

(Continued)

*Primary Examiner* — Carl H Layno
*Assistant Examiner* — Jennifer Ghand

(57) ABSTRACT

A method and system for tracking quality of life in a patient with angina includes obtaining activity data and cardiac data, determining a level of physical activity of the patient and identifying an ischemic episode based on the cardiac data obtained during the physical activity. The method also provides for recording an activity level at the time the ischemic episode occurs. Furthermore, the method also provides for presenting activity level trends related to activity levels at the onset of ischemia to a user.

23 Claims, 7 Drawing Sheets

U.S. PATENT DOCUMENTS

| | | |
|---|---|---|
| 2005/0027321 A1 | 2/2005 | Ferek-Petric |
| 2005/0059897 A1 | 3/2005 | Snell et al. |
| 2006/0009811 A1 | 1/2006 | Sheldon et al. |
| 2006/0116593 A1 | 6/2006 | Zhang et al. |
| 2007/0208263 A1* | 9/2007 | John et al. .................. 600/509 |
| 2008/0177191 A1 | 7/2008 | Patangay et al. |
| 2008/0177194 A1* | 7/2008 | Zhang et al. ................ 600/513 |
| 2008/0183086 A1* | 7/2008 | Song et al. .................. 600/508 |
| 2008/0208069 A1* | 8/2008 | John et al. .................. 600/509 |

FOREIGN PATENT DOCUMENTS

| | | |
|---|---|---|
| WO | 0057781 | 10/2000 |
| WO | 03020366 A1 | 3/2003 |
| WO | 03020367 A1 | 3/2003 |
| WO | 2004047917 A1 | 6/2004 |
| WO | 9834537 | 2/2005 |
| WO | 20080091529 | 2/2005 |

\* cited by examiner

METHOD AND SYSTEM FOR TRACKING QUALITY OF LIFE IN PATIENTS WITH ANGINA

FIELD OF THE INVENTION

Embodiments of the present invention pertain generally to implantable medical devices, and more particularly pertain to methods and systems that utilize a patient's activity level and occurrence of angina pain to trend the progression of ischemia in the patient.

BACKGROUND OF THE INVENTION

Many patients at risk of cardiac ischemia have pacemakers, implantable cardioverter defibrillators (ICDs), or other medical devices implanted therein. Electrocardiograms (ECG) are useful for diagnosing ischemia and locating damaged areas within the heart. Cardiac ischemia is a condition whereby heart tissue does not receive adequate amounts of oxygen and is usually caused by a blockage of an artery leading to heart tissue. ECGs are composed of various waves and segments that represent the heart depolarizing and repolarizing. The ST segment represents the portion of the cardiac signal between ventricular depolarization and ventricular repolarization. While P-waves, R-waves and T-waves may be generally considered features of a surface ECGs, for convenience and generality, herein the terms R-wave, T-wave and P-wave are also used to refer to the corresponding internal cardiac signal, such as an intra-cardiac electrogram (IEGM).

Techniques have been developed for detecting cardiac ischemia using implanted medical devices. Some conventional IEGM-based ischemia detection techniques seek to detect ischemia by identifying changes in the elevation of the ST segment from the baseline of the IEGM that occur during cardiac ischemia. Elevation of the ST segment in an IEGM may result when there are abnormalities in the polarizations of cardiac tissue during an acute myocardial infraction (AMI). Deviation of the ST segment from a baseline is a result of injury to cardiac muscle, changes in the synchronization of ventricular muscle depolarization, drug or electrolyte influences, or the like. However, not all ST segment shifts are indicative of AMI or other injury to the cardiac muscle. Instead, a ST segment shift above or below the baseline may result because of "axis shifts", electrical noise, cardiac pacing, high sinus or tachycardia cardiac rates that distort the IEGM waveform.

Heretofore, conventional pacemakers or defibrillators have experienced some difficulties in identifying ST segment shifts that are not indicative of AMI, ischemia or other injury to the myocardial muscle. One type of ischemia is "demand ischemia" which becomes apparent when the oxygen demand increases sufficiently. Demand ischemia will often lead to anginal pain, such as during physical exertion. The anginal pain is often associated with a predictable threshold of physical activity. Hence, a patient may experience chest pains (e.g., angina) while exercising. Conventional IMDs do not monitor any relation between patient activity and ischemic condition, nor provide any indication of how much activity a patient endures before suffering anginal pain.

A need exists for methods and systems to track a patient's level of activity before the onset of anginal pain and/or ischemia. Additionally, a need remains for methods and systems determining the level of activity a patient may endure over a period of time without suffering from anginal pain.

SUMMARY

In accordance with at least one embodiment, a method is provided for tracking quality of life in a patient with angina. The method includes obtaining activity data and determining when a level of physical activity of the patient reaches a predetermined state. The method further includes obtaining cardiac data and identifying an ischemic episode based on the cardiac data obtained during the physical activity. The method also provides for recording an activity level associated with the ischemic episode and presenting trend information related to the activity levels. For example, the trend information may include activity level trend data points and/or a number of occurrences of angina pain.

Optionally, the method may provide for identifying the ischemic episode by assessing a level of angina pain, where the level of angina pain is based on a relation between the activity level and an ischemic episode. The method further identifies a level of physical activity as a level of activity having a sustained duration over a predetermined period of time. For instance, in one embodiment, the level of physical activity is greater than a predetermined threshold level. In one embodiment, the activity level may include a running average of a plurality of activity level data points. The method also provides commencing physical activity by having the patient inform an implantable medical device (IMD) that exercise will begin by tapping on the body.

In accordance with another embodiment, a system is provided for tracking quality of life in a patient with angina. The system includes a memory, a processor and an output. The memory stores cardiac signals representative of cardiac activity having ST segment variation and stores activity data for a patient over a time period the patient is exercising above a predetermined threshold value. The processor is configured to determine when a level of physical activity of the patient reaches a predetermined state, identify an ischemic episode based on the cardiac data obtained during the physical activity, and record the activity level associated with the ischemic episode; the output displays trend information related to the activity levels, such as activity trend data values and/or a number of occurrences of angina pain.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
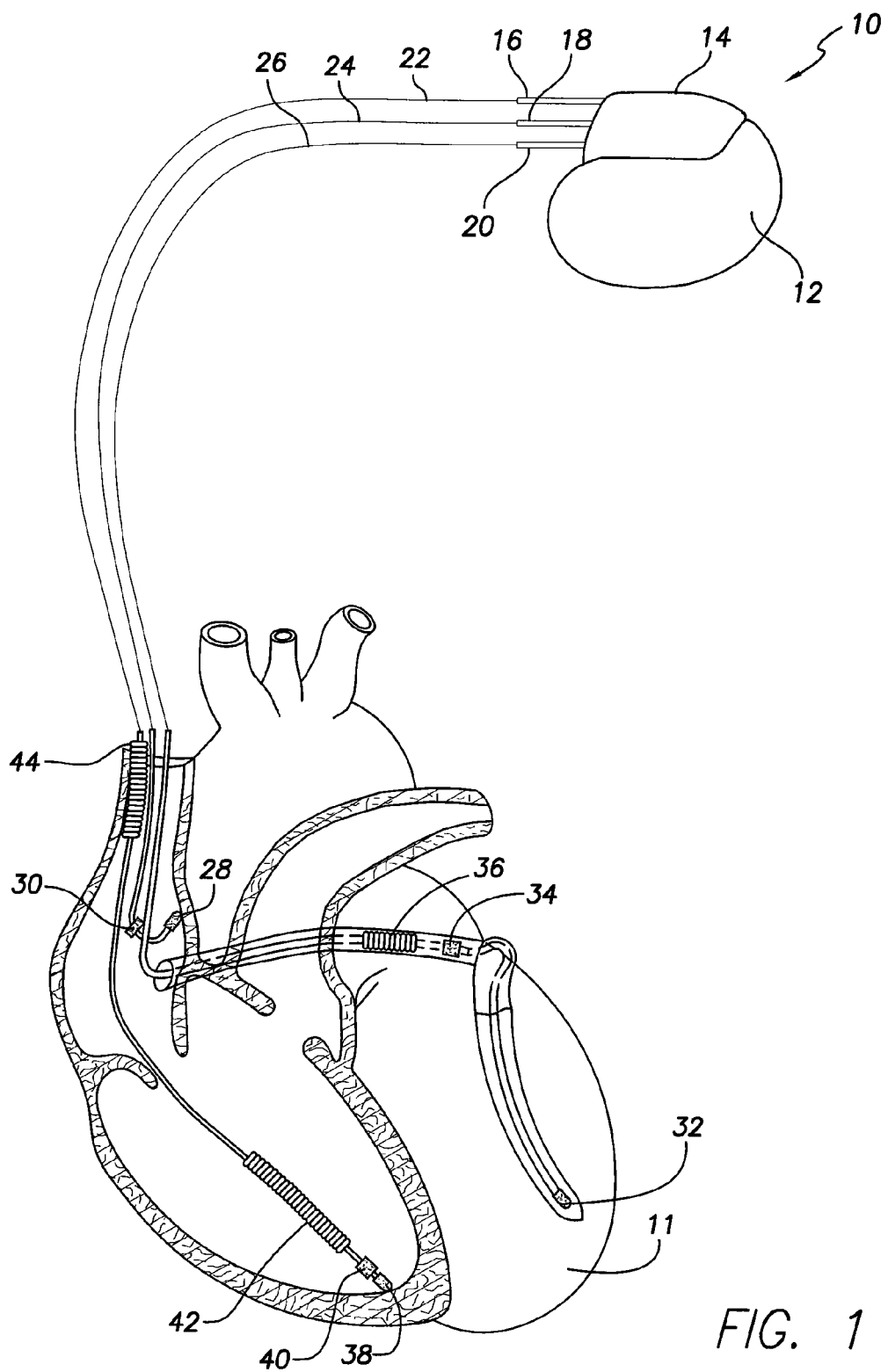
FIG. 1 illustrates an implantable medical device formed in accordance with an embodiment of the present invention.

FIG. 1 illustrates an implantable medical device 10 (IMD) that is coupled to a heart 11. The implantable medical device 10 may be a cardiac pacemaker, an implantable cardioverter defibrillator ("ICD"), a defibrillator, or an ICD coupled with a pacemaker. The IMD 10 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 10 may be controlled to monitor cardiac signals and based thereof, to identify potentially abnormal physiology (e.g., ischemia) when a patient exerts a level of physical activity greater than a predetermined threshold or exerts themselves for a predetermined period of time at a particular level. The detected cardiac signals may include intrinsic heart beats that have no assistance from any type of manmade electrical stimulation. Alternatively, the detected cardiac signals may include heart beats that have been stimulated by an electrical source to produce a paced heartbeat. The electrical source that provides the paced heartbeat may include an implantable device that provides low energy electrical signals, such as provided by a pacemaker, a demand pacemaker, a single-chamber pacemaker, a dual chamber pacemaker, a biventricular pacemaker, and the like. Optionally, the paced heartbeat may be generated by an implantable device that provides high energy electrical signals such as those provided by an implantable cardioverter defibrillator.

The IMD 10 includes a housing 12 that is joined to a header assembly 14 (e.g., an IS-4 connector assembly) that holds receptacle connectors 16, 18, and 20 that are connected to a right ventricular lead 22, a right atrial lead 24, and a coronary sinus lead 26, respectively. The leads 22, 24 and 26 may be located at various locations, such as an atrium, a ventricle, or both to measure the physiological condition of the heart 11. One or more of the leads 22, 24 and 26 detect intra-cardiac electrogram signals that form an electrical activity indicator of myocardial function over multiple cardiac cycles. To sense atrial cardiac signals and to provide right atrial chamber stimulation therapy, the right atrial lead 24 having at least an atrial tip electrode 28, which is typically implanted in the right atrial appendage, and an atrial ring electrode 30. The IEGM signals represent analog signals that are subsequently digitized and analyzed to identify waveforms of interest. Examples of waveforms identified from the IEGM signals include the P-wave, T-wave, the R-wave, the QRS complex and the like. The waveforms of interest may be collected over a period of time, either continuously or at defined intervals.

The coronary sinus lead 26 receives atrial and ventricular cardiac signals and delivers left ventricular pacing therapy using at least a left ventricular tip electrode 32. Left atrial pacing therapy may use at least a left atrial ring electrode 34. Optionally, a left atrial coil electrode 36 may deliver one or both of a pacing and/or shock therapy. The right ventricular lead 22 has a right ventricular tip electrode 38, a right ventricular ring electrode 40, a right ventricular (RV) coil electrode 42, and a SVC coil electrode 44. Therefore, the right ventricular lead 22 is capable of receiving cardiac signals, and delivering stimulation in the form of pacing and shock therapy to the right ventricle.

IMD 10 may be used to collect cardiac signals (e.g., both intrinsic and paced heart beats). Initially, the IMD 10 may collect baseline cardiac signals and microcontroller 60 (shown in FIG. 2) may determine ST segment variations for the baseline signals. The baseline cardiac signals and ST segment variations may be stored in memory 94 (shown in FIG. 2). The IMD 10 may be reprogrammed by a programmer (shown in FIG. 3) in order for the IMD 10 to properly monitor the cardiac signals and provide the correct paced heartbeat. The IMD 10 may obtain cardiac signals (e.g., IEGM) on a beat-by-beat basis and store each heart beat in memory 94 (shown in FIG. 2). In addition, associated with each heart beat, IMD 10 may store the time the heart beat occurred and the heart rate of the heart beat. Microcontroller 60 may determine the ST segment variation associated with the heart beat and store the ST segment value in memory 94.

Figure 2:
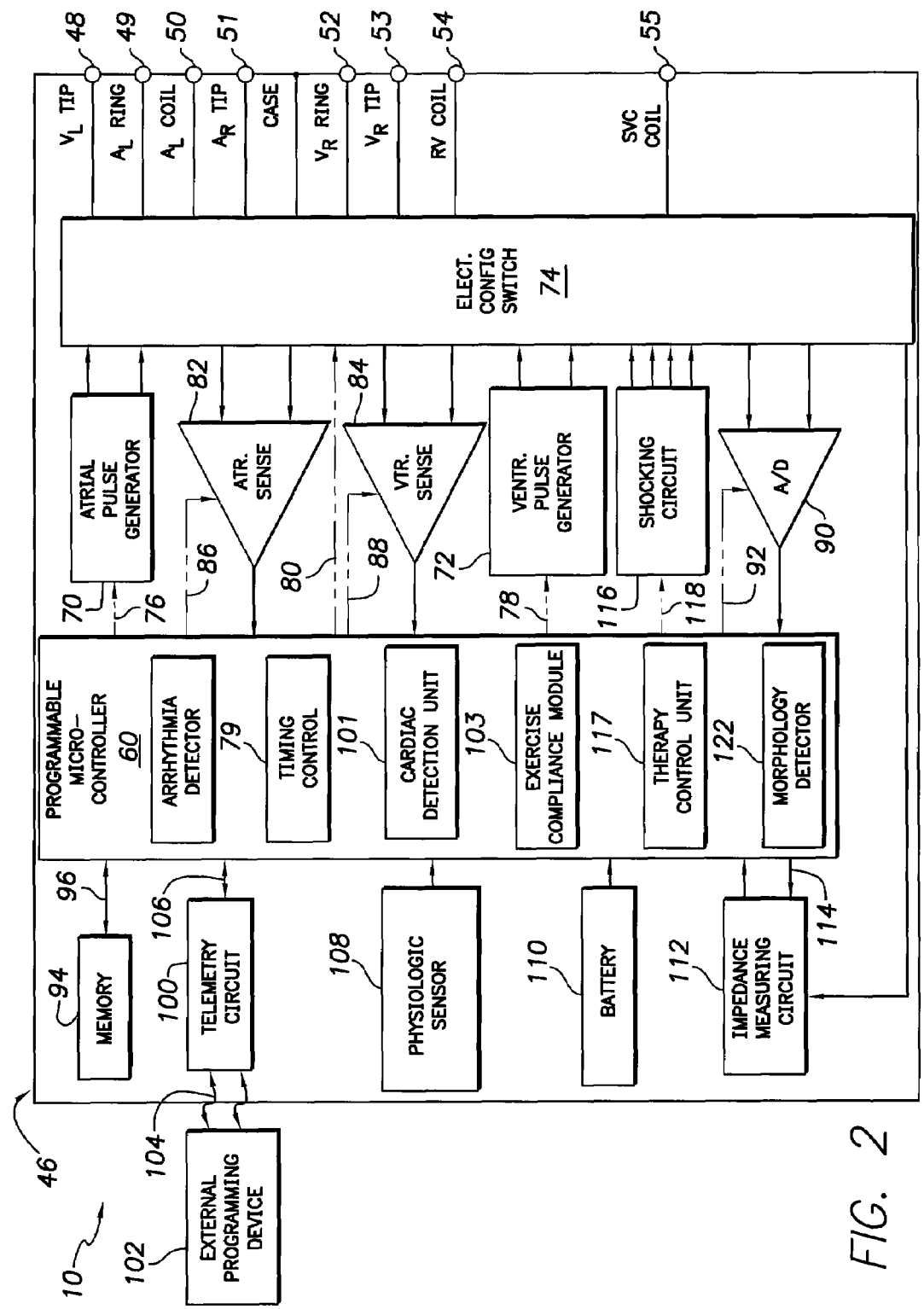
FIG. 2 illustrates a functional block diagram of exemplary internal components of an implantable medical device formed in accordance with an embodiment of the present invention.

Furthermore, the IMD 10 may be used to measure various levels of physical activity of the patient through a physiological sensor 108 (shown in FIG. 2). As a patient begins exerting themselves (e.g., exercising), the physiological sensor 108 (e.g., an accelerometer) may measure a level of physical activity. The microcontroller 60 may determine when the level of activity may be greater than a predetermined threshold value and determine a relationship of the level of physical activity to an occurrence of anginal pain and associated ischemia.

FIG. 2 illustrates a block diagram of exemplary internal components of the IMD 10. The IMD 10 is for illustration purposes only, and it is understood that the circuitry could be duplicated, eliminated or disabled in any desired combination to provide a device capable of treating the appropriate chamber(s) of the heart with cardioversion, defibrillation and/or pacing stimulation.

The housing 46 for IMD 10 (shown schematically in FIG. 2), is often referred to as the "can", "case" or "case electrode" and may be programmably selected to act as the return electrode for all "unipolar" modes. The housing 46 further includes a connector (not shown) having a plurality of terminals, namely a right atrial tip terminal ($A_R$ TIP) 51, a left ventricular tip terminal ($V_L$ TIP) 48, a left atrial ring terminal ($A_L$ RING) 49, a left atrial coil terminal ($A_L$ COIL) 50, a right ventricular tip terminal ($V_R$ TIP) 53, a right ventricular ring terminal ($V_R$ RING) 52, a right ventricular shocking terminal ($R_V$ COIL) 54, and an SVC shocking terminal (SVC COIL) 55.

The IMD 10 includes a programmable microcontroller 60, which controls the operation of the IMD 10 based on acquired cardiac signals. For example, the microcontroller 60 includes a cardiac detection unit 101 to monitor the cardiac signals and to identify therein ST segment shifts and determine potential ischemic and AMI conditions. The microcontroller 60 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. The microcontroller 60 also includes an exercise compliance module 103 that senses and processes activity data from a physiologic sensor 108. In one embodiment the physiologic sensor 108 may be an accelerometer, an activity sensor, a piezo-electric sensor, workload sensor, or any type of sensor that measures metabolic changes. The activity data may include body movements of the patient, senses metabolic changes (e.g., such as nutrition and oxygen consumption of the patient), heart rate, and pacing levels. The exercise compliance module 103 may determine when the patient is in a state of sustained exercise, such as when the level of activity (e.g., when the patient is exercising) is greater than a predetermined threshold value. Alternatively, the exercise compliance module 103 may identify sustained exercise based on the duration of the activity. For instance, when the patient has been exerting themselves at a constant level for an extended period of time, but has not reached the predetermined threshold level, the activity level may be deemed sufficient to be characterized as sustained exercise. Optionally, the exercise compliance module 103 may declare a sustained exercise state when the activity level increases by a set amount within a short period of time.

The exercise compliance module 103 may interact with the cardiac detection unit 101 as the patient exercises to determine, for example, the changes in blood pressure, heart rate, and paced heart rate. As the patient exercises, changes in ST segment may be monitored by the cardiac detection unit 101. As an ST deviation or ST shift is determined, as described below, the occurrence of an ischemic event (e.g., ischemia, demand ischemia, AMI and the like) may be provided to the exercise compliance module 103 in order to determine and store in memory 94, a value of the activity level at the time the ischemic event occurred. The activity level trend values may be presented graphically and may be superimposed over a number of occurrences of ischemia in a particular day.

The microcontroller 60 may also analyze the data, for example, in connection with collecting, over a period of time, reference ST segment shifts in a cardiac signal (e.g., sense signals received from leads 22, 24 and 26). The microcontroller 60 may measure ST segment shifts and compare the ST shifts to a ST threshold to identify a potential abnormal physiology (e.g., such as when the patient is having a post-myocardial infarct, a "silent" myocardial infarct, a myocardial infarct, an ischemia, a heart block, an arrhythmia, fibrillation, congestive heart failure, and the like).

The IMD 10 includes an atrial pulse generator 70 and a ventricular pulse generator 72 to generate pacing stimulation pulses. The pulse generators 70 and 72 are controlled by microcontroller 60 via appropriate control signals 76 and 78, respectively, to trigger or inhibit the stimulation pulses. Switch 74 includes a plurality of switches for connecting the desired electrodes to the appropriate I/O circuits, thereby providing complete electrode programmability. Atrial sensing circuits 82 and ventricular sensing circuits 84 may also be selectively coupled to the leads through the switch 74 for detecting the presence of cardiac activity in each of the four chambers of the heart. Control signals 86 and 88 from processor 60 direct output of the atrial and ventricular sensing circuits 82 and 84 that are connected to the microcontroller 60.

The cardiac signals are applied to the inputs of an analog-to-digital (A/D) data acquisition system 90. The cardiac signals may be IEGM signals or ECG signals. The data acquisition system 90 is configured to acquire IEGM signals, convert the raw analog data into digital IEGM signals, and store the digital IEGM signals in memory 94 for later processing and/or telemetric transmission to an external device 102. Memory 94 may also store a variable threshold value 120 and a ST threshold 122. Control signal 92 from microcontroller 60 determines when the A/D 90 acquires signals, stores them in memory 94 or transmits data to an external device 102. The data acquisition system 90 is coupled to the right atrial lead 24, the coronary sinus lead 26, and the right ventricular lead 22 through the switch 74 to sample cardiac signals across any combination of desired electrodes.

The cardiac detection unit 101 receives the cardiac signals from A/D 90 and determines the onset and determination of an ischemic or AMI condition based on a ST segment deviation. The cardiac cycle is composed of a P-wave, a Q-wave, an R-wave, an S-wave, and a T-wave. The portion of the signal between the S-wave and T-wave constitutes a ST segment. The ST segment may have a voltage level that aligns with the voltage level of a baseline heart rhythm. Alternatively, the ST segment may have a voltage level that is shifted above or shifted below the baseline. ST segment variations indicate a potential coronary episode. ST segment variations may include ST deviations or ST shifts. A ST deviation is determined by subtracting an average PQ segment (e.g., the iso-electric segment) voltage from the ST segment voltage for a heartbeat. The ST deviation provides a measure of the change in variability over a period of time. A ST shift is determined by changes in the ST deviation over a period of time. For example, a current ST shift may be calculated by subtracting a stored baseline ST deviation from a newly acquired ST deviation. ST deviations and ST shifts may be calculated as averages over multiple cardiac cycles as well.

The discrimination of ischemia related and non-ischemia related shifts in the ST segment may be determined by the cardiac detection unit 101 by using a statistical determination of the variability of the ST segment shift. For example, a plurality of ST segment shifts may be collected to obtain a ST threshold. Then the ST threshold is used in a comparison with subsequently measured ST segment shifts to identify the onset of a coronary episode. When the measured ST segment shift is less than a ST threshold, the termination of the coronary episode may be identified. Upon detecting the onset of a coronary episode, either an ischemic event or an AMI event, the cardiac signals (e.g., IEGM or EGM) are stored in memory 94.

The microcontroller 60 is coupled to the memory 94 by a suitable data/address bus 96, wherein the programmable operating parameters used by the microcontroller 60 are stored and modified, as required, in order to customize the operation of IMD 10 to suit the needs of a particular patient. The memory 94 may store activity level data as the patient commences exercising. The activity level data may include a heart rate, a pacing rate, a blood pressure, a respiratory rate, changes in body posture, and the like. The memory 94 may also store data indicative of myocardial function, such as the IEGM data, ST segment shifts, reference ST segment shifts, and the like for a desired period of time (e.g., one hour, 24 hours, one month, and the like). Memory 94 may also store large amounts of data in order to determine ischemic detection parameters. For instance, memory 94 may store raw cardiac data, from both intrinsic heart beats and paced heart beats, which is used to generate baseline cardiac signals. Memory 94 may store the baseline cardiac signals and may also store updates to each baseline cardiac signal. In addition, activity data may be stored in memory 94. The memory 94 may also store instructions that direct the microcontroller 60 to analyze the cardiac data to detect ischemia and/or to identify events of interest. In addition, memory 94 may store instructions to direct microcontroller 60 to determine a level of physical activity of a patient, identify an ischemic episode based on the cardiac data obtained during the physical activity, and record the activity level at the time the ischemic episode occurs. For example, memory 94 may store instructions to direct microcontroller 60 to count the number of ischemia-related ST variations that accrue in each of a series of heart rate ranges over a trend period.

The operating parameters of the IMD 10 may be non-invasively programmed into the memory 94 through a telemetry circuit 100 in communication with the external device 102, such as a programmer (shown in FIG. 3), trans-telephonic transceiver or a diagnostic system analyzer. The telemetry circuit 100 is activated by the microcontroller 60 by a control signal 106. The telemetry circuit 100 allows intracardiac electrograms, and status information relating to the operation of IMD 10 (as contained in the microcontroller 60 or memory 94) to be sent to the external device 102 through an established communication link 104.

The IMD 10 additionally includes a battery 110, which provides operating power to all of the circuits shown within the housing 46, including the processor 60. The IMD 10 is shown as having an impedance measuring circuit 112 which is enabled by the microcontroller 60 via a control signal 114. The impedance measuring circuit 112 is advantageously coupled to the switch 74 so that impedance at any desired electrode may be obtained.

Figure 3:
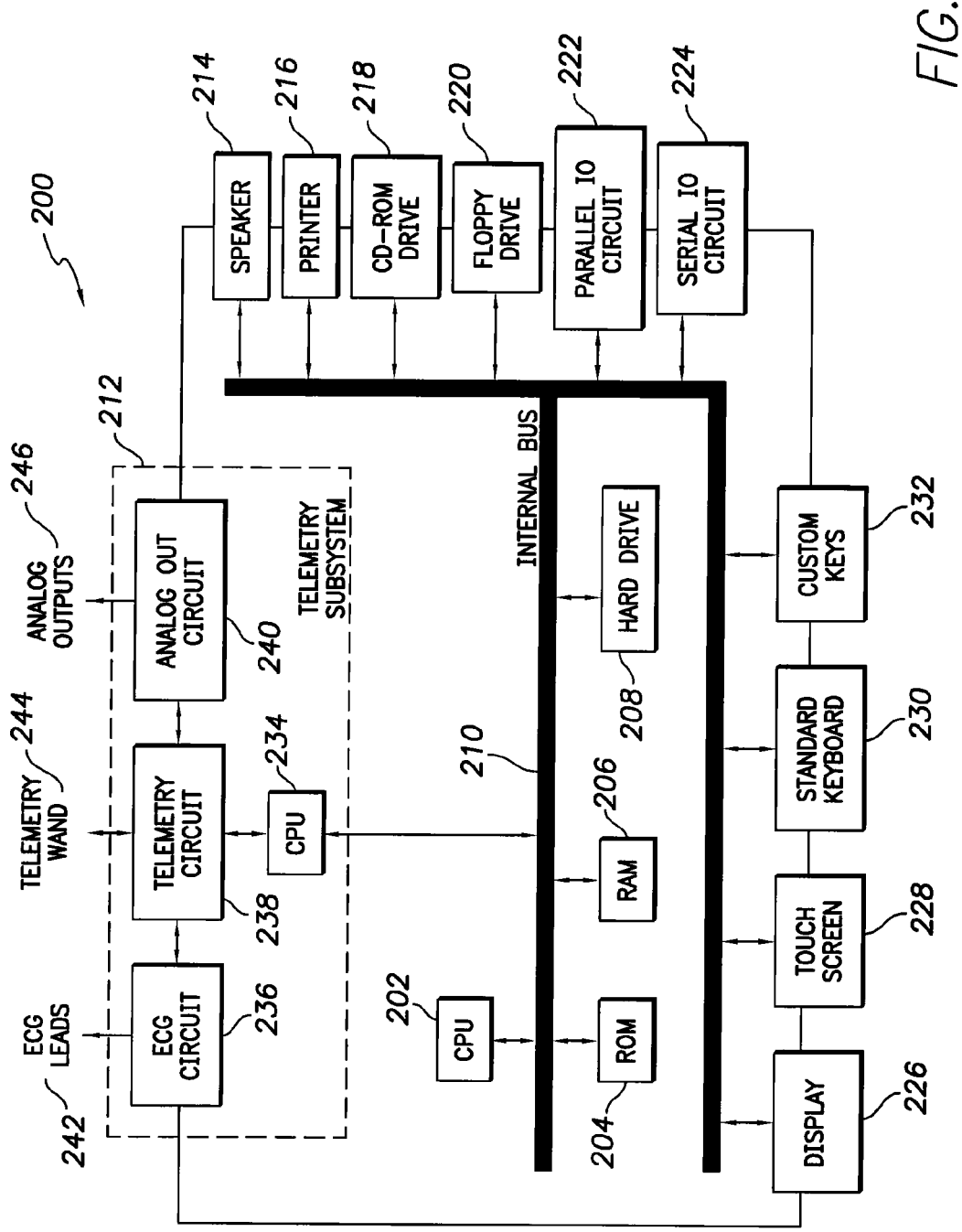
FIG. 3 illustrates a functional block diagram of certain components of an external programmer used to communicate with the implantable medical device shown in FIG. 1 utilized in accordance with an embodiment of the present invention.

FIG. 3 illustrates a functional block diagram of an external device 200, such as a programmer, that is operated by a physician, a health care worker, or a patient to interface with IMD 10. The external device 200 may be utilized in a hospital setting, a physician's office, or even the patient's home to communicate with the IMD 10. Further, the external device 200 may be utilized to interrogate the IMD 10 to determine the condition of a patient, to adjust the physiological parameters monitored, or to change the therapy. For example, the external device 200 may obtain activity level data, activity level thresholds, cardiac data, ischemia trend values, activity level trend values, and the like, from the IMD 10. The external device 200 may be used to monitor in real-time the heart beat (e.g., intrinsic as well as paced) as collected by the surface ECG unit 342.

The external device 200 may store the raw cardiac information (e.g., cardiac signals, associated heart rate, time the heart beats occurred, and the like) received from IMD 10 or ECG unit 342 in RAM 206 or hard drive 208. Alternatively, the external device 200 may transfer the raw cardiac information as well as the activity data via the telemetry subsystem 212 to IMD 10 or via the internet 336 (shown in FIG. 4) to a database 324 for storage. The external device 200 may process the cardiac and activity data to obtain ischemia and activity trend values which are then stored and/or displayed. Optionally, the external device 200 may transfer the raw cardiac information (e.g., cardiac signals, activity level data, ischemia trend values, activity level trend values, and the like) via the internet 336 (shown in FIG. 4) to a user workstation 346 or server 332 for processing and trending. External device 200 includes an internal bus 210 that connects/interfaces with a Central Processing Unit (CPU) 202, ROM 204, RAM 206, a hard drive 208, a speaker 214, a printer 216, a CD-ROM drive 218, a floppy drive 220, a parallel I/O circuit 222, a serial I/O circuit 224, a display 226, a touch screen 228, a standard keyboard connection 230, custom keys 232, and a telemetry subsystem 212.

In order for a physician or health care worker to communicate with the external device 200, a display 226, a touch screen 228, a standard keyboard 230, and custom keys 232 are provided. The display 226 (e.g., may be connected to a video display) and the touch screen 228 may display text, alphanumeric information, data and graphic information via a series of menu choices to be selected by the user relating to the IMD 10. For example, a user may select status information, operating parameters, therapy parameters, patient status, access settings, software programming version, and the like. The display 226 may present activity level related trends, such as discussed below in connection with FIGS. 6 and 7. The display 226 may present a graph of the activity level of the patient, as a statistical average of the activity level, along with a number of occurrences of ischemia during a particular day to be presented to a physician. Alternatively, the display 226 may present the activity level trend of the patient. The touch screen 228 accepts a user's touch input when selections are made. The keyboard 230 (e.g., a typewriter keyboard) allows the user to enter data as well as interface with the telemetry subsystem 212.

The telemetry subsystem 212 may be used to communicate with IMD 10. The telemetry subsystem 212 includes a central processing unit (CPU) 234 in electrical communication with a telemetry circuit 238, which communicates with both an ECG circuit 236 and an analog out circuit 240. The ECG circuit 236 is connected to ECG leads 242, the telemetry circuit 238 is connected to a telemetry wand 244, and the analog out circuit 212 includes communication circuits, such as a transmitting antenna, modulation and demodulation stages (not shown), as well as transmitting and receiving stages (not shown) to communicate with analog outputs 246. The external device 200 may wirelessly communicate with the IMD 10 and utilize protocols, such as Bluetooth, GSM, infrared wireless LANs, HIPERLAN, 3G, satellite, as well as circuit and packet data protocols, and the like.

Figure 4:
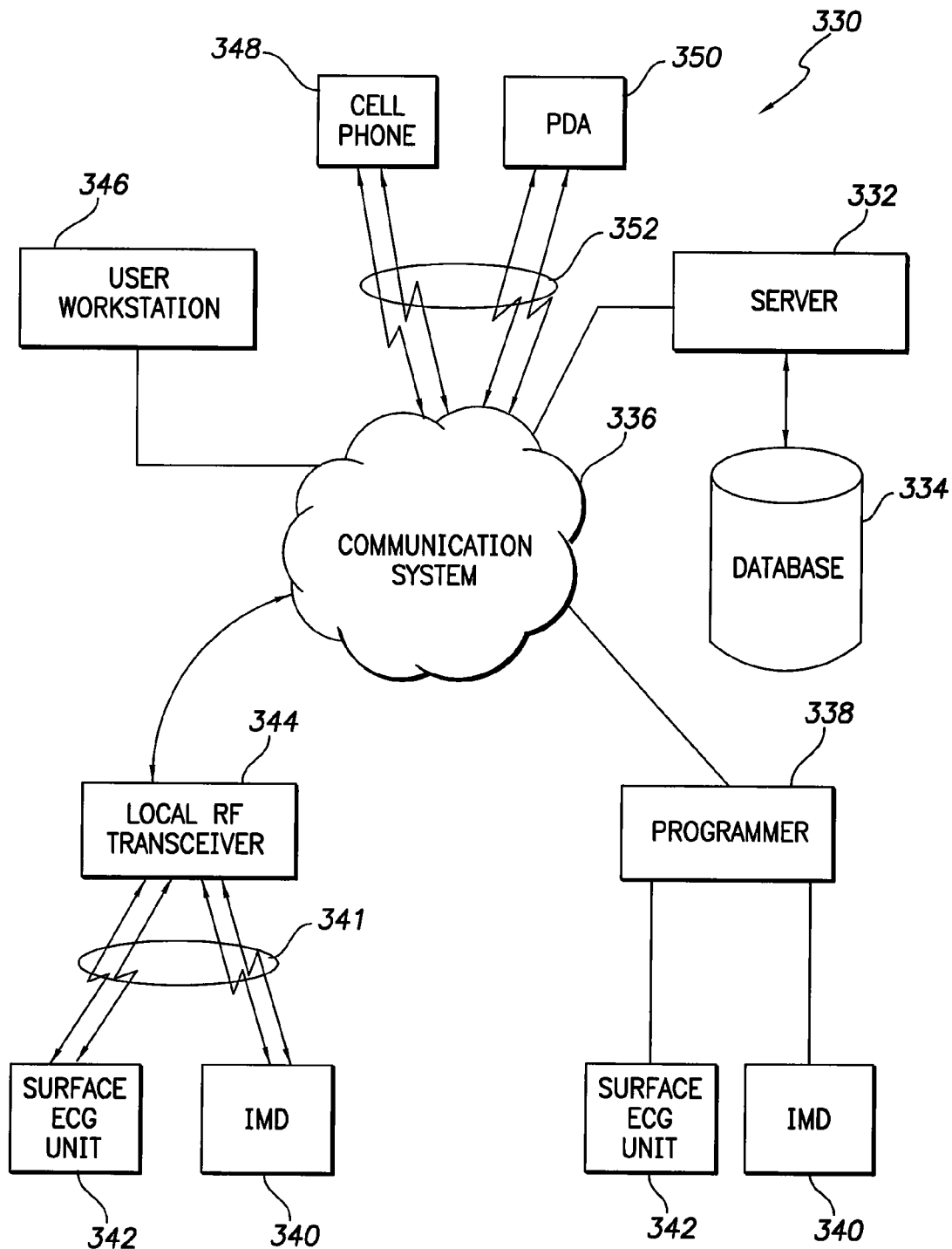
FIG. 4 illustrates a functional block diagram of a distributed processing system utilized in accordance with an embodiment of the present invention.

FIG. 4 illustrates a distributed processing system 330 that may present activity and ischemia related trends. The distributed processing system 330 includes a server 332 that is connected to a database 334, a programmer 338 (e.g. similar to external device 200 described above), a local RF transceiver 344 and a user workstation 346 electrically connected to a communication system 336 (e.g., such as the internet, a voice over IP ("VoIP") gateway, a public switched telephone network ("PSTN"), a local area network ("LAN"), and the like). The server 332 controls the transmission and reception of information (e.g., cardiac signals, activity level data, processed cardiac signals, ST segments, histograms, statistical analysis, trend lines, and the like). The server 332 interfaces with the communication system 336 to store/retrieve cardiac and activity level information between the programmer 338, the local RF transceiver 344, the user workstation 346, a cell phone 348, and a personal data assistant ("PDA") 350 to the database 334. The server 332 may process the activity level data to produce an activity level trend line related to the value of the activity level at the time an ischemic event occurs. The server 332 may store the processed information in local memory or in database 334, and the server 332 may display the results of processed activity level data (e.g., trend information), as well as any cardiac signals, on the user workstation 346, the cell phone 348, the PDA 350 or, optionally, the programmer 338.

Database 334 stores information such as activity level data, an activity threshold value, duration of an activity, statistical information regarding the activity level data (e.g., average value of activity level data for a day), activity level data at the time of an ischemia, cardiac signals, processed cardiac signals, statistical calculations, histograms, cardiac trends (e.g., ST segment trends), a ST variation baseline, ST variation trend data points, ischemia trend values, and the like. The database 334 may also store activity level data, an activity baseline, activity trend data points, and activity trends, which are based on, for example, body heart rates, pacing rates, motion, body fluids, muscular sounds, nutrition consumption, nutritional changes, metabolic changes, and the like.

The programmer 338 is similar to the external device 200 described above and may reside in a patient's home, a hospital, or a physician's office. Programmer 338 interfaces with a surface ECG unit 342 and an IMD 340 (e.g., similar to ICD 10 described above). In one embodiment, the ECG unit 342 may acquire activity data from an activity sensor (e.g., accelerometer) that senses body movements of the patient. The activity sensor may be a workload sensor, a physiological sensor, or any other type of sensor that senses metabolic changes, such as nutrition and oxygen consumption of the patient. The programmer 338 may wirelessly communicate 341 with the IMD 340. Alternatively, a hard-wired connection may be used to connect the programmer 338 to IMD 340 (e.g., an electrical cable having a USB connection). The programmer 338 is able to acquire cardiac signals from the surface of a person (e.g., ECGs) or the programmer may acquire intra-cardiac electrograms (e.g., IEGMs) from IMD 340. The programmer 228 may collect a plurality of cardiac signals (e.g., intrinsic and paced) along with timing information, ST segment information, and heart rate information that is used to determine ST variances. The programmer 338 may be used to collect the cardiac signals from either the surface ECG unit 342 or the IMD 340, and then the programmer 338 may process the cardiac signals. Alternatively, the programmer 338 may interface with the communication system 336 to transfer the raw cardiac information (e.g., cardiac signals, heart rates, ST segment value, and the like) as well as activity level data, activity level thresholds, and activity level trends over the communication system 336 to be stored in database 334 or to be processed by the server 332 or the user workstation 346.

The local RF transceiver 334 may be located in a patient's home and may function to provide an interface to the surface ECG unit 342 and the IMD 340 to communicate to server 332, programmer 338, or the user workstation 346 over communication system 336. In one embodiment, the surface ECG unit 342 and the IMD 340 have a bi-directional connection with the local RF transceiver via a wireless connection 341. The local RF transceiver 334 may upload the activity and cardiac data acquired from the surface ECG unit 342 or the IMD 340 via the communication system 336 to the server 332, the programmer 338, or the user workstation 346 for additional processing to determine trend information. Alternatively, the local RF transceiver 334 may internally process the cardiac and activity data to determine the trend information and a potential ischemic condition. The local RF transceiver 334 may transmit the trend information via communications system 336 to be displayed on the user workstation 346, the cell phone 348, or PDA 350.

The user workstation 346 may interface with the communication system 336 to download activity level and cardiac information via the server 332 from the database 334. Alternatively, the user workstation may download in real-time activity level and cardiac data from the surface ECG unit 342 or IMD 340 via either the programmer 338 or the local RF transceiver 344. After downloaded the cardiac information (e.g., raw cardiac signals) and activity level data the user workstation 346 may process the cardiac signals and activity level data immediately or at a later time period to create histograms, calculate statistical parameters, determine cardiac trends, and activity level trends to determine if the patient is suffering from an ischemia. The user workstation 346 may download the resulting trend information and potential ischemic condition to the cell phone 348, the PDA 350, the local RF transceiver 344, the programmer 338, or to the server 332 to be stored on the database 334.

Figure 5:
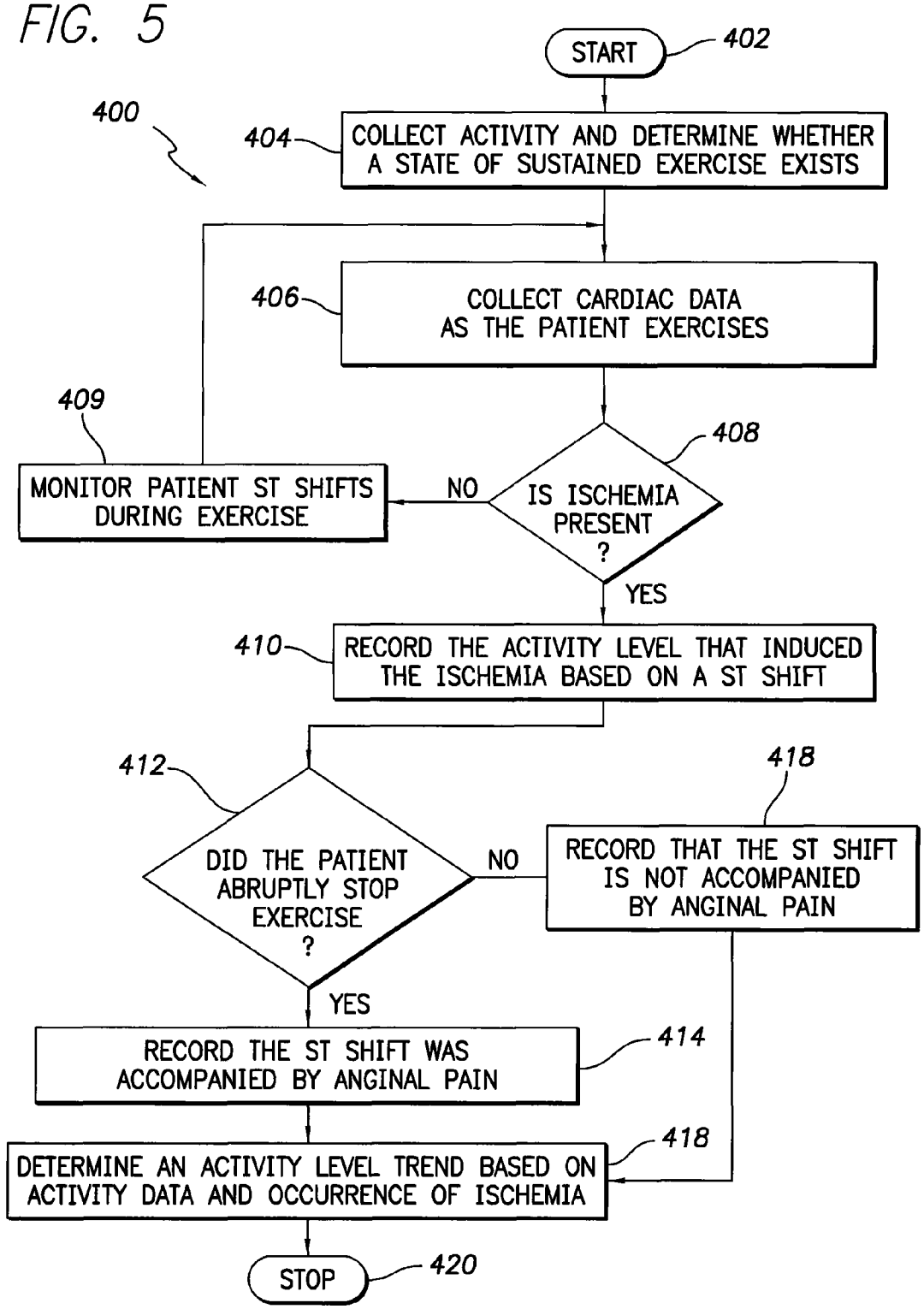
FIG. 5 illustrates a flow diagram for a method for presenting activity level trends utilized in accordance with an embodiment of the present invention.

FIG. 5 illustrates a flow diagram for a series of operations for a process 400 that tracks quality of life in a patient with angina and presents activity level trends in accordance with an embodiment of the present invention. The process 400 may be implemented by one or more of the devices and systems of FIGS. 1-4. At 402, the process commences.

At 404, the process begins by acquiring patient activity data over a predetermined period of time (e.g., an hour, four hours, eight hours, a day and the like). The activity may be measured by using the physiological sensor 108 (shown in FIG. 2). For instance, an accelerometer or an activity sensor may be used to sense body movements of the patient. Alternatively, the activity sensor may be a workload sensor or any other type of sensor that senses metabolic changes, such as nutrition and oxygen consumption of the patient. At 404, the activity data is analyzed to determine whether a state of sustained exercise has been achieved. The state of sustained exercise is declared when the level of activity is greater than a predetermined exercise threshold value (e.g., greater than 130% of at rest level). Alternatively, the sustained exercise state may be described when the activity level is less than the predetermined exercise threshold value, but the activity level remains at an intermediate threshold level for a predetermined length of time (e.g., at 75% of the exercise threshold value for a sustained duration of five minutes, 20 minutes and the like). As a further alternative, the sustained exercise state may be declared when the activity level increases by a large incremental amount in a short period of time. The activity data may be stored in memory 94 for later retrieval and processing.

Optionally, the activity level data may be compared to an activity level baseline value. The baseline of the activity level data may be determined over a predetermined period of time (e.g., one hour). The activity level data, to determine the baseline, may be collected when the patient is minimally exerting herself. For example, a patient may be walking at a non-exercise pace for the baseline predetermined period of time. The baseline may be an average of multiple values of a patient's activity over multiple predetermined periods of time (e.g., one hour periods measured weekly). Alternatively, the baseline activity may be acquired only once in a longer period of time (e.g., once every six months) while the activity level data is acquired more often.

At 406, as the patient exercises, cardiac data, which includes ST segments, are acquired. The cardiac data is collected over a series of cardiac cycles for a predetermined period of time. For instance, the cardiac data may be collected over a ten minute or one hour sample interval. The cardiac data may be a series of intrinsic heartbeats. Alternatively, the cardiac data may be a series of paced heartbeats, which are stimulated by either an atrial pulse generator or a ventricular pulse generator. Further, the cardiac data may be collected before, concurrently with, or after the activity data in step 404.

A ST baseline may be determined based on the ST segment variations in the cardiac data. The ST segment variations may be caused by abnormalities in the polarizations of cardiac tissue during an acute myocardial infraction. ST segment variations may arise because of differences in the electric potential between cells that have become ischemic and those cells that are still receiving normal blood flow. ST segment variations may be an indication of injury to cardiac muscle, changes in the synchronization of ventricular muscle depolarization, drug or electrolyte influences, or the like. The ST baseline may be determined by collecting cardiac data when the patient is resting and not moving (e.g., sitting or laying down). The baseline may be based on data collected over a baseline predetermined period of time (e.g., an hour, four hours, a day and the like).

At 408, microcontroller 60 monitors the cardiac data for ST segment variations, such as ST shifts and ST deviations, as described above, and check for any ischemic episodes (e.g., ischemia, demand ischemia, AMI, an inconsistent physiology, and the like). If no ischemic episode has occurred, flow continues to step 409, to continue monitoring cardiac data for ST segment variations as the patient continues to exercise. If an ischemic episode occurs, flow continues to step 410.

At 410, the activity level that induced the ischemia may be recorded in memory 94. Alternatively, an activity level that is a running average of activity level data from the time of beginning exercise or from the time of the last ischemic episode may be recorded. Further activity data may be recorded at the time of the ischemic episode, such as, heart rate, pacing rate, blood pressure, respiratory rate, oxygen consumption, carbon-dioxide production, body motion, and the like. At 412, microcontroller 60 checks if the patient abruptly stopped exercising. For example, microcontroller 60 monitors the physiologic sensor 108 (e.g., accelerometer) for any significant measurement drop over a predetermined window of time (e.g., the measurement drop may be based on a percentage drop). For instance, the patient may have stopped exercising immediately upon having the ischemic episode because of anginal pain (e.g., a change in body posture immediately following an ischemic episode). Alternatively, the patient may indicate an amount of anginal pain by tapping their body proximate to the IMD location. If the patient stopped exercising after the ischemic episode, at 414, the process 400 records in memory 94 that the ST shift is accompanied by anginal pain. However, if the patient did not stop exercising during the ischemic episode, at 416, the process 400 records in memory 94 that the ST shift is not accompanied by anginal pain. After recording whether there was an occurrence of anginal pain, the flow continues to step 418.

At 418, microcontroller 60 determines an activity level data point based on the activity level value at the occurrence of the ischemic episode. Alternatively, the activity level data point may represent a running average of the activity level when the ischemic episode occurred. Over a predetermined period of time (e.g., several months), an activity level trend may be determined based on a plurality of activity level data points. A graph of a running average of the activity level of the patient and the number of occurrences of anginal pain are presented to a physician. The running average of activity level and number of occurrences of anginal pain may be presented as being overlaid on one another. Alternatively, the running average of activity level and the number of occurrences of anginal pain may be co-displayed. At 420, the process 400 terminates and may be repeated.

Figure 6:
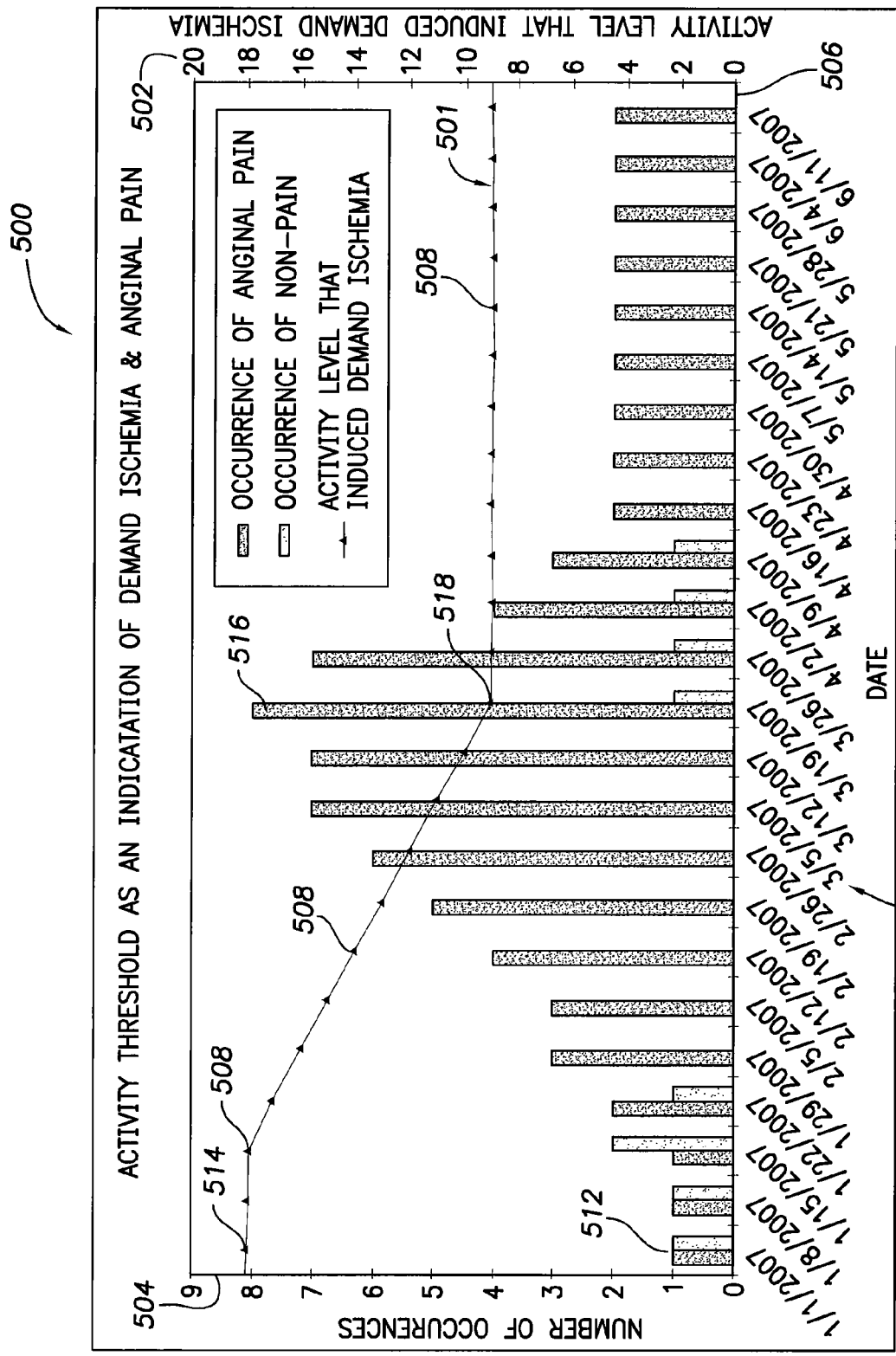
FIG. 6 illustrates a graph of an activity level trend depicting a patient adapting activity to compensate for anginal pain formed in accordance with an embodiment of the present invention.
Figure 7:
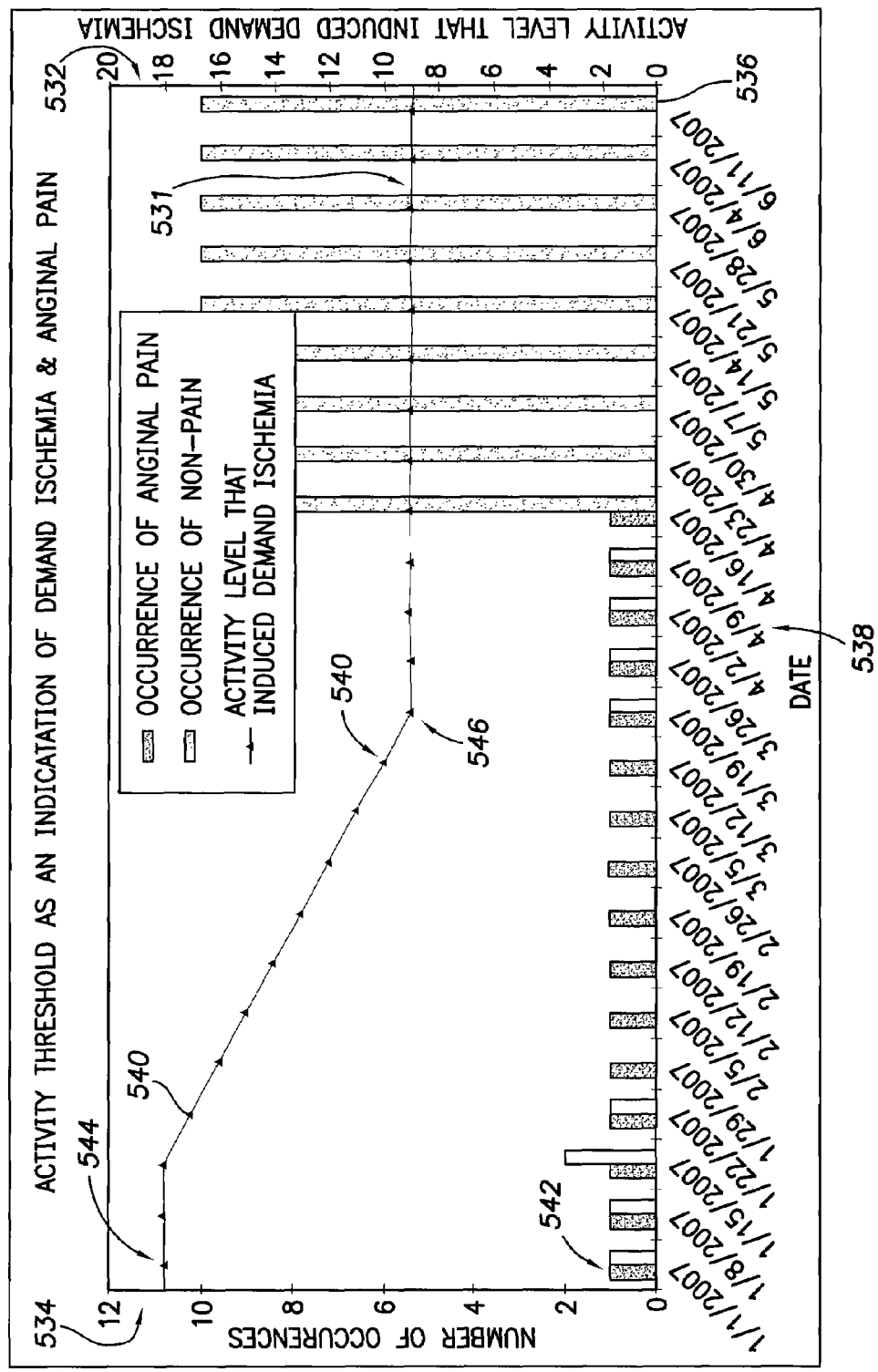
FIG. 7 illustrates a graph of an activity level trend for a patient whose threshold for an ischemic event is decreasing formed in accordance with an embodiment of the present invention.

FIGS. 6 and 7 illustrate exemplary formats for presenting trend information as graphs 500 and 530 of a patient's activity level trends 501 and 531 associated with a number of occurrences of anginal pain. The presentation may include displaying the graph on a display (e.g., computer, video, touch screen), producing a hard copy (e.g., paper), a PDA 350, a cell phone 348, a workstation 346, a monitor, an external programming device 102, and the like. Graph 500 includes a left vertical axis that plots the number of occurrences of anginal pain 504, a right vertical axis that plots a patient activity level 502, and a horizontal axis that plots dates 506. Graph 500 depicts, for example, a twenty-four week trend (e.g., January through June) having an activity level for one day each week. For each specific day 510, an activity level data point 508 is provided that represents a running average of patient activity level 502 for the day 510. The value of the activity level data point 508 may be an average of the measured activity level for each occurrence of anginal pain for a particular day. For instance, on Jan. 1, 2007, there was one occurrence of anginal pain 512 with a corresponding activity level data point 514 having a value of 18. Furthermore, from January to March, the number of occurrences of anginal pain increased. On Mar. 19, 2007, the number of occurrences of anginal pain reached a maximum value 516 (e.g., 8) with a corresponding decrease in activity level 518 (e.g., an activity level value of 9). Each of the eight occurrences of anginal pain had a corresponding activity level value. The activity level data point 518 value may be determined by taking an average of each of the activity level values for the eight occurrences of anginal pain. The correlation of the occurrence of anginal pain 504 with patient activity level 502 may indicate the occurrence of ischemia. In the example of FIG. 6, the activity level trend 501 indicates a decrease of activity level 502 as the occurrence of anginal pain 504 increases over a predetermined period of time, which may indicate the advancement of coronary artery disease.

Similarly, FIG. 7 illustrates a graph 530 depicting an activity level trend 531. Graph 530 includes a left vertical axis that plots the number of occurrences of anginal pain 534, a right vertical axis that plots a patient activity level 532, and a horizontal axis that plots dates 536. Graph 530 depicts, for example, a twenty-four week trend (e.g., January through June) having an activity level for one day each week. For each specific day 538, an activity level data point 540 may be provided that represents a running average of patient activity level 532 for that day 538. The value of the activity level data point 540 may be an average of the measured activity level for each occurrence of anginal pain for a particular day. Each activity level data point 540 is a running average of patient activity level 532 at the time of an occurrence of anginal pain 534 for a specific day 538. For example, FIG. 7 shows on Jan. 1, 2007, the number of occurrences of anginal pain 542 (e.g., one) with a corresponding activity level 544 value of 18. The number of occurrences of anginal pain remain constant through Apr. 16, 2007 (e.g., having one occurrence of anginal pain for each day plotted on graph 530) with a corresponding decrease in physical activity level. For example, the activity level value started on January 1 having a value of 18 as shown by activity level data point 544, and the activity level decreased over time to a value of 9 on March 19, as shown by activity level data point 546. From March 19 through June 11, the activity level trend value remains at a constant value of 9. Thus, FIG. 7 represents a graph 530 of an activity trend level 531 that may indicate that coronary artery disease may not be affecting a patient's ability to exercise.

Optionally, the activity level trend data may be presented without the occurrence of anginal pain. Alternatively, the activity level trend data may be presented in formats, such as candle-stick charts, pie charts, multiple graphs, color coded graphs, color-coded bar charts and the like. In various embodiments of the invention, the method for presenting patient activity level trend associated with the occurrence of anginal pain in addition to other trends can be implemented in software, hardware, or a combination thereof. The methods provided by various embodiments of the present invention, for example, can be implemented in software by using standard programming languages such as, for example, C, C++, Java, and the like.

In accordance with certain embodiments, methods and systems for tracking quality of life in a patient with angina are provided. Activity level data and cardiac data are obtained. An activity level trend is determined based on the patient's activity level at the onset of anginal pain. The activity level trend values and a number of occurrences of anginal pain are co-displayed to a user.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

While the invention has been described in terms of various specific embodiments, those skilled in the art will recognize that the invention can be practiced with modification within the spirit and scope of the claims.

What is claimed is:

1. A method for tracking quality of life in a patient with angina, said method comprising:
   obtaining activity data and cardiac data over multiple sample intervals within a trending period of time;
   determining, based on the activity data for each of the sample intervals, whether a level of physical activity of the patient reaches a predetermined state;
   identifying an ischemic episodes based on the cardiac data for the corresponding sample intervals in which the level of the physical activity reaches the predetermined state;
   recording an activity level associated with each of the ischemic episodes; and
   presenting trend information indicating the activity levels and a number of the ischemic episodes over the trending period of time, wherein the trend information includes a graph that plots the activity levels and number of ischemic episodes along first and second axes and time along a third axis.

2. The method of claim 1, wherein the level of physical activity is a level of activity having a sustained duration over a predetermined period of time.

3. The method of claim 1, wherein the activity data comprises a plurality of activity level data points, each of which represents a running average of the level of physical activity for the corresponding sample interval.

4. The method of claim 1, wherein the level of physical activity is greater than a predetermined threshold level.

5. The method of claim 1, wherein the level of physical activity is a steadily increasing level of activity over a predetermined period of time.

6. The method of claim 1, wherein an activity level comprises a graph of a plurality of activity level data points for a corresponding sample interval over the trending period of time.

7. The method of claim 1, wherein the recording comprises monitoring a duration of each of the ischemic episodes until the patient stops exercising.

8. A method comprising:
   monitoring for an ischemic event during a time when an activity level of a patient satisfies a predetermined condition;
   if an ischemic event is detected, recording activity data associated with the detected ischemic event; and
   performing the monitoring and recording operations over multiple sample intervals within a trending period of time and presenting trend information indicating the recorded activity data and a number of the ischemic episodes over the trending period of time, wherein the trend information includes a graph that plots the activity levels and number of ischemic episodes along first and second axes and time along a third axis.

9. The method of claim 8 wherein monitoring for an ischemic event during a time when an activity level of a patient satisfies a predetermined condition comprises:
   obtaining activity data for the patient; and
   determining the activity level of the patient based on the activity data.

10. The method of claim 8 wherein activity data corresponds to measurements of at least one of heart rate, pacing rate, blood pressure, respiratory rate, oxygen consumption, carbon-dioxide production, body posture and body motion.

11. The method of claim 8 wherein activity data associated with the detected ischemic event comprises an activity data measured at the time of ischemic event detection.

12. The method of claim 8 wherein activity data associated with the detected ischemic event comprises an average of a plurality of activity data, one of which is measured at the time of ischemic event detection.

13. The method of claim 8 wherein the predetermined condition comprises a sustained activity level for a predetermined period of time.

14. The method of claim 8 wherein the predetermined condition comprises an activity level at or above a predetermined threshold level.

15. The method of claim 8 wherein the predetermined condition comprises an activity level that steadily increases over a predetermined period of time.

16. The method of claim 8 further comprising determining whether the ischemic event corresponds to demand ischemia.

17. The method of claim 16 wherein determining whether the ischemic event corresponds to demand ischemia comprises monitoring for an abrupt decrease in activity level.

18. The method of claim 16 wherein determining whether the ischemic event corresponds to demand ischemia comprises receiving an indication of anginal pain through physical movement of an implantable medical device.

19. The method of claim 16 further comprising maintaining a measure of the occurrences of demand ischemia and non-demand ischemia.

20. The method of claim 19 wherein the measure comprises a count of occurrences during a time period.

21. The method of claim 8 wherein trend information comprises a measure of ischemic events as a function of activity data.

22. The method of claim 21 wherein the measure of ischemic events is a count of ischemic events during a corresponding sample interval and the activity data is an average of the recorded activity data corresponding to the ischemic events during a corresponding sample interval.

23. The method of claim 22 wherein the count of ischemic events comprise a count of demand ischemic events and a count of non-demand ischemic events during the corresponding sample interval.

* * * * *